(12) United States Patent
Ault et al.

(10) Patent No.: US 7,049,283 B2
(45) Date of Patent: May 23, 2006

(54) PHARMACEUTICAL COMPOSITIONS FOR THE ORAL DELIVERY OF PHARMACOLOGICALLY ACTIVE AGENTS

(75) Inventors: Joseph M. Ault, Blairstown, NJ (US); Moise Azria, Basel (CH); Simon David Bateman, Randolph, NJ (US); Joseph Sikora, Succasunna, NJ (US); Gregory Sparta, Bridgewater, NJ (US); Rebecca Fai-ying Yang, Randolph, NJ (US); Jie Xiao, Randolph, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/006,311

(22) Filed: Dec. 4, 2001

(65) Prior Publication Data

US 2002/0123459 A1     Sep. 5, 2002

Related U.S. Application Data

(60) Provisional application No. 60/251,729, filed on Dec. 6, 2000.

(51) Int. Cl.
*A01N 37/18*     (2006.01)

(52) U.S. Cl. .......................................... 514/2
(58) Field of Classification Search ............... 514/2; 424/725
See application file for complete search history.

(56) References Cited

U.S. PATENT DOCUMENTS

| | | |
|---|---|---|
| 5,002,771 A | 3/1991 | Purkaystha et al. |
| 5,015,633 A | 5/1991 | Sudilovsky .................. 514/91 |
| 5,681,811 A | 10/1997 | Ekwuribe |
| 5,756,450 A | 5/1998 | Hahn et al. .................... 514/9 |
| 5,773,647 A | 6/1998 | Leone-Bay et al. ......... 562/444 |
| 5,866,536 A | 2/1999 | Leone-Bay et al. ............ 514/2 |
| 5,958,453 A | 9/1999 | Ohno et al. ................. 424/465 |
| 5,972,381 A | 10/1999 | Sangekar et al. |
| 2002/0065255 A1* | 5/2002 | Bay et al. |

FOREIGN PATENT DOCUMENTS

| | | |
|---|---|---|
| EP | 0438147 A2 | 7/1991 |
| GB | 2 295 966 A | 6/1996 |
| NZ | 507275 | 11/2001 |
| WO | WO 99/47196 | 9/1999 |
| WO | WO 00 57857 | 10/2000 |
| WO | WO 00/59863 | 10/2000 |

OTHER PUBLICATIONS

Abstract, Database Biosis, Leone-Bay et al., "Oral delivery of biologically active parathyroid hormone," Pharmaceutical Research (NY), vol. 18(7), pp. 964-970 (2001).

* cited by examiner

*Primary Examiner*—Michael Meller
(74) *Attorney, Agent, or Firm*—Peter J. Waibel; E. Jay Wilusz

(57) ABSTRACT

Solid pharmaceutical compositions suitable for the oral delivery of pharmacologically active agents, e.g. peptides, comprising a therapeutically-effective amount of a pharmacologically active agent; a crospovidone or povidone; and a delivery agent for said pharmacologically active agent are disclosed. The compositions provide excellent oral bioavailability of pharmacologically active agents, particularly calcitonin.

3 Claims, No Drawings

PHARMACEUTICAL COMPOSITIONS FOR THE ORAL DELIVERY OF PHARMACOLOGICALLY ACTIVE AGENTS

This application claims benefit of Provisional Application No. 60/251,729, filed on Dec. 6, 2000.

BACKGROUND OF THE INVENTION

1. Field of the Invention

The present invention relates to oral compositions for the delivery of pharmacologically active agents, to methods of enhancing the bioavailability of orally administered pharmacologically active agents, and to methods of treating and/or preventing disease in mammals, particularly humans, by orally administering a pharmacologically active agent in accordance with the invention.

2. Description of the Related Art

Oral delivery of pharmacologically active agents is generally the delivery route of choice since it is convenient, relatively easy and generally painless, resulting in greater patient compliance relative to other modes of delivery. However, biological, chemical and physical barriers such as varying pH in the gastrointestinal tract, powerful digestive enzymes, and active agent impermeable gastrointestinal membranes, makes oral delivery of some pharmacologically active agents to mammals problematic, e.g. the oral delivery of calcitonins, which are long-chain polypeptide hormones secreted by the parafollicular cells of the thyroid gland in mammals and by the ultimobranchial gland of birds and fish, has proven difficult due, at least in part, to the insufficient stability of calcitonin in the gastrointestinal tract as well as the inability of calcitonin to be readily transported through the intestinal walls into the blood stream.

U.S. Pat. Nos. 5,773,647 and 5,866,536 describe compositions for the oral delivery of active agents, such as heparin and calcitonin, with modified amino acids, such as, N-(5-chlorosalicyloyl)-8-aminocaprylic acid (5-CNAC), N-(10-[2-hydroxybenzoyl]aminodecanoic acid (SNAD), and N-(8-[2-hydroxybenzoyl]amino)caprylic acid (SNAC) In addition, WO 00/059863 discloses the disodium salts of formula I

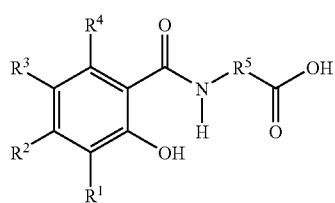

Formula I wherein $R^1$, $R^2$, $R^3$, and $R^4$ are independently hydrogen, —OH, —$NR^6R^7$, halogen, $C_1$–$C_4$alk $C_1$–$C_4$alkoxy;

$R^5$ is a substituted or unsubstituted $C_2$–$C_{16}$alkylene, substituted or unsubstituted $C_2$–$C_{16}$alkenylene, substituted or unsubstituted $C_1$–$C_{12}$alkyl(arylene), or substituted or unsubstituted aryl($C_1$–$C_{12}$alkylene); and $R^6$ and $R^7$ are independently hydrogen, oxygen, or $C_1$–$C_4$ alkyl; and hydrates and solvates thereof as particularly efficacious for the oral delivery of active agents, such as calcitonin, cyclosporin and heparin.

The present invention describes pharmaceutical compositions which provide still greater oral bioavailability of pharmacologically active agents, e.g. peptides such as calcitonin.

SUMMARY OF THE INVENTION

Accordingly, the present invention is directed to pharmaceutical compositions which, quite surprisingly, greatly enhance the oral bioavailability of active agents, particularly peptides. Specifically, the invention provides solid pharmaceutical compositions suitable for the oral delivery of pharmacologically active agents, comprising 1. a therapeutically-effective amount of a pharmacologically active agent;
2. a crospovidone or povidone; and
3. a delivery agent for said pharmacologically active agent.

In another embodiment the present invention provides solid pharmaceutical compositions suitable for the oral delivery of calcitonin, comprising 1. a therapeutically-effective amount of a calcitonin; and
2. a crospovidone or povidone;

In a further embodiment, the invention is directed to a method for enhancing the oral bioavailability of a pharmacologically active agent, said method comprising administering to a subject in need of said pharmacologically active agent an effective amount of a pharmaceutical composition according to the instant invention.

In a still further embodiment, the invention is directed to a method of treatment of bone related diseases and calcium disorders comprising administering to a patient in need of such treatment a therapeutically effective amount of a composition according to the instant invention, wherein said pharmacologically active agent is calcitonin.

Further features and advantages of the invention will become apparent from the following detailed description of the invention.

DETAILED DESCRIPTION OF THE INVENTION

The pharmacologically active agents suitable for use in the instant invention include both therapeutic as well as preventative agents and is directed particularly to agents which by themselves do not pass or which pass only a small amount of the administered dose through the gastro-intestinal mucosa and/or are susceptible to cleavage by acids and enzymes in the gastro-intestinal tract. The pharmacologically active agents include, but are not limited to proteins; polypeptides; hormones; polysaccharides including mixtures of muco-polysaccharides; carbohydrates; lipids; and combinations thereof.

Specific examples of pharmacologically active agents include, but are not limited to, the following, including synthetic, natural or recombinant sources thereof: growth hormone, including human growth hormones (hGH), recombinant human growth hormones (rhGH), bovine growth hormones, and porcine growth hormones; growth hormone-releasing hormones; interferons, including α, β, and γ-interferon; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low, very low and ultra low molecular weight heparins; calcitonin, including salmon, porcine, eel, chicken and human; erythopoietein; atrial naturetic factor; antigens; monoclonal antibodies; somatostatin; protease inhibitors; adrenocorticotropin, gonadotropin releasing hormone; oxytocin; leutinizing-hormone-releasing hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof.

The preferred pharmacologically active agent is a pharmacologically active peptide, particularly calcitonin. A known class of pharmacologically active agents, calcitonins have varying pharmaceutical utility and are commonly employed in the treatment of e.g. Paget's disease, hypercalcemia and postmenopausal osteoporosis. Various calcitonins, including salmon, pig and eel calcitonin are commercially available and commonly employed for the treatment of e.g. Paget's disease, hypercalcemia of malignancy and osteoporosis. The calcitonin can be any calcitonin, including natural, synthetic or recombinant sources thereof, as well as calcitonin derivatives such as 1,7-Asu-eel calcitonin. The compositions can comprise a single calcitonin or any combination of two or more calcitonins. The preferred calcitonin is synthetic salmon calcitonin.

The calcitonins are commercially available or may be synthesized by known methods.

The amount of pharmacologically active agent is generally an amount effective to accomplish the intended purpose, e.g. a therapeutically effective amount. However, the amount can be less than that amount when a plurality of the compositions are to be administered, i.e., the total effective amount can be administered in cumulative dosage units. The amount of active agent can also be more than the effective amount when the composition provides sustained release of the pharmacologically active agent. The total amount of active agent to be used can be determined by methods known to those skilled in the art. However, because the compositions may deliver the active agent more efficiently than prior compositions, less amounts of active agent than those used in prior dosage unit forms or delivery systems can be administered to a subject while still achieving the same blood levels and/or therapeutic effects.

When the pharmacologically active agent is salmon calcitonin, the appropriate dosage will, of course, vary depending upon, for example, the host and the nature and severity of the condition being treated. However, in general, satisfactory results will be obtained systemically at daily dosages of from about 0.5 µg/kg to about 10 µg/kg animal body weight, preferably 1 µg/kg to about 6 µg/kg body weight.

The pharmacologically active agent generally comprises from 0.05 to 70 percent by weight relative to the total weight of the overall pharmaceutical composition, preferably an amount of from 0.01 to 50 percent by weight, more preferably 0.3 to 30 percent by weight relative to the total weight of the overall pharmaceutical composition.

The crospovidone can be any crospovidone. Crospovidone is a synthetic crosslinked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. The preferred crospovidone is Polyplasdone XL.

Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP.

As mentioned above, the crospovidones and povidones are commercially available. Alternatively, they may be synthesized by known processes.

The crospovidone, povidone or combination thereof is generally present in the compositions in an amount of from 0.5 to 50 percent by weight relative to the total weight of the overall pharmaceutical composition, preferably an amount of from 2 to 25 percent, more preferably 5 to 20 percent by weight relative to the total weight of the pharmaceutical composition.

The delivery agents useful in the present invention are any agents useful for delivering the particular pharmacologically active agent. Suitable delivery agents are any one of the 123 modified amino acids disclosed in aforementioned U.S. Pat. No. 5,866,536 or any one of the 193 modified amino acids described in the aforementioned U.S. Pat. No. 5,773,647 or any combination thereof. The contents of the aforementioned U.S. Pat. Nos. 5,773,647 and 5,866,536 are hereby incorporated by reference in their entirety. In addition, the delivery agent can be the disodium salt of any of the aforementioned modified amino acids as well as ethanol solvates and hydrates thereof. Suitable compounds include compounds of the following formula I

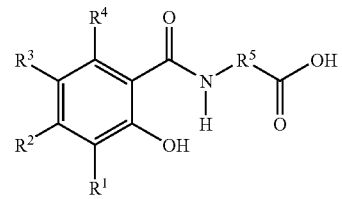

Formula I wherein $R^1$, $R^2$, $R^3$, and $R^4$ are independently hydrogen, —OH, —NR$^6$R$^7$, halogen, $C_1$–$C_4$alkyl, or $C_1$–$C_4$alkoxy, $R^5$ is a substituted or unsubstituted $C_2$–$C_{16}$alkylene, substituted or unsubstituted $C_2$–$C_{16}$alkenylene, substituted or unsubstituted $C_1$–$C_{12}$alkyl(arylene), or substituted or unsubstituted aryl($C_1$–$C_{12}$alkylene); and $R^6$ and $R^7$ are independently hydrogen, oxygen, or $C_1$–$C_4$ alkyl; and hydrates and alcohol solvates thereof. The compounds of formula I as well as their disodium salts and alcohol solvates and hydrates thereof are described in WO 00/059863, along with methods for preparing them.

The disodium salt may be prepared from the ethanol solvate by evaporating or drying the ethanol solvate by methods known in the art to form the anhydrous disodium salt. Drying is generally carried out at a temperature of from about 80 to about 120° C., preferably from about 85 to about 90° C., and most preferably at about 85° C. The drying step is generally performed at a pressure of 26" Hg or greater. The anhydrous disodium salt generally contains less than about 5% by weight of ethanol and preferably less than about 2% by weight of ethanol, based on 100% total weight of anhydrous disodium salt.

The disodium salt of the delivery agent can also be prepared by making a slurry of the delivery agent in water and adding two molar equivalents of aqueous sodium hydroxide, sodium alkoxide or the like. Suitable sodium alkoxides include, but are not limited to, sodium methoxide, sodium ethoxide, and combinations thereof.

A still further method of preparing the disodium salt is by reacting the delivery agent with one molar equivalent of sodium hydroxide to yield the disodium salt.

The disodium salt can be isolated as a solid by concentrating the solution containing the disodium salt to a thick paste by vacuum distillation. This paste may be dried in a vacuum oven to obtain the disodium salt of the delivery agent as a solid. The solid can also be isolated by spray drying an aqueous solution of the disodium salt.

The delivery agents may be prepared by methods known in the art, e.g., as mentioned above, by methods described in U.S. Pat. Nos. 5,773,647 and 5,866,536.

The ethanol solvates, as described in the aforementioned WO 00/059863, include, but are not limited to, a molecular or ionic complex of molecules or ions of ethanol solvent with molecules or ions of the disodium salt of the delivery agent. Typically, the ethanol solvate contains about one ethanol molecule or ion for every molecule of disodium salt of the delivery agent.

The ethanol solvate of the disodium salt of the delivery agent can be prepared by dissolving the delivery agent in ethanol. Typically, each gram of delivery agent is dissolved in from about 1 to about 50 mL of ethanol and generally, from about 2 to about 10 mL of ethanol. The delivery agent/ethanol solution is then reacted with a molar excess of a sodium containing salt, such as a monosodium containing salt, relative to delivery agent, i.e. for every mole of delivery agent there is more than one mole of sodium cations, yielding the ethanol solvate. Suitable monosodium salts include, but are not limited to, sodium hydroxide; sodium alkoxides, such as sodium methoxide and sodium ethoxide; and any combination of the foregoing. Preferably, at least about two molar equivalents of the monosodium containing salt are added to the ethanol solution, i.e. for every mole of delivery agent there is at least about two moles of sodium cations. Generally, the reaction is performed at or below the reflux temperature of the mixture, such as at ambient temperature. The ethanol solvate is then recovered by methods known is the art, such as, concentration of the resulting slurry at atmospheric distillation, cooling the concentrated slurry and filtering the solid. The recovered solid can then be vacuum dried to obtain the ethanol solvate.

The hydrates of the disodium salts of the delivery agents may be prepared by drying the ethanol solvate to form an anhydrous disodium salt, as described above, and hydrating the anhydrous disodium salt. Preferably, the monohydrate of the disodium salt is formed. Since the anhydrous disodium salt is very hydroscopic, the hydrate forms upon exposure to atmospheric moisture. Generally, the hydrating step is performed at from about ambient temperature to about 50° C., preferably ambient temperature to about 30° C. and in an environment having at least 50% relative humidity. Alternatively, the anhydrous disodium salt may be hydrated with steam.

The preferred delivery agents are N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAC) and their monosodium and disodium salts, ethanol solvates of their sodium salts and the monohydrates of their sodium salts and any combinations thereof. The most preferred delivery agent is the disodium salt of 5-CNAC and the monohydrate thereof.

The pharmaceutical compositions of the present invention typically contain a delivery effective amount of one or more of the delivery agents, i.e. an amount sufficient to deliver the active agent for the desired effect. Generally, the delivery agent is present in an amount of 2.5% to 99.4% by weight, more preferably 25% to 50% by weight.

The pharmaceutical compositions of the present invention may be provided as a capsule including a soft-gel capsule, tablet, caplet or other solid oral dosage form, all of which can be prepared by methods well known in the art.

The compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102 supplied by FMC corporation, or any combination thereof. Other additives may include phosphate buffer salts, citric acid, glycols, and other dispersing agents.

The composition may also include one or more enzyme inhibitors, such as actinonin or epiactinonin and derivatives thereof; aprotinin, Trasylol and Bowman-Birk inhibitor.

Further, a transport inhibitor, i.e. a p-glycoprotein such as Ketoprofin, may be present in the compositions of the present invention.

Preferably, the solid pharmaceutical compositions of the instant invention include a diluent, such as Avicel, and a lubricant, such as magnesium stearate.

The solid pharmaceutical compositions of the instant invention can be prepared by conventional methods e.g. by blending a mixture of the active agent or active agents, the delivery agent, the crospovidone or povidone and other ingredients, kneading, and filling into capsules or, instead of filling into capsules, molding followed by further tableting or compression-molding to give tablets. In addition, a solid dispersion may be formed by known methods followed by further processing to form a tablet or capsule.

Preferably, the ingredients in the pharmaceutical compositions of the instant invention are homogeneously or uniformly mixed throughout the solid dosage form.

The compositions of the present invention may be administered to deliver an active agent to any animal in need thereof, including, but not limited to, mammals, such as rodents, cows, pigs, dogs, cats, and primates, particularly humans.

The following examples serve to further illustrate the invention.

EXAMPLE 1

Tablets were prepared in accordance with the present invention (EXAMPLE A) as well as COMPARATIVE EXAMPLES B AND C which utilize Ac-Di-Sol in place of the crospovidone (Ac-Di-Sol is cross-linked carboxymethylcellulose sodium) and COMPARATIVE EXAMPLE D, which is a colyophilized capsule containing 5-CNAC and salmon calcitonin.

Specifically, the tablets are prepared as follows:

PREPARATION OF EXAMPLE A 0.502 of salmon calcitonin, pre-screened through a 40 mesh screen, 120 g of CNAC disodium salt, pre-screened through a 35 mesh screen, and 20 g of Polyplasdone XL (crospovidone, NF) is combined in a 500 mL jar and is mixed using a Turbula mixer for 2 minutes at a speed of 46 RPM. An additional 125.4 g of 5-CNAC disodium salt, pre-screened through a 35 mesh screen, and 32.5 g of Avicel PH 102 is added to the jar and is mixed for a period of 8 minutes at a speed of 46 RPM. A further 32.5 g of Avicel is added to the jar and is mixed for 5 minutes at a speed of 46 RPM. 4.0 g of magnesium stearate is screened into the jar using a 35 mesh screen and is blended for 1 minute at a speed of 46 RPM. The final blend is compressed into tablets using a Manesty B3B tablet press. The tablet weight is approximately 400 mg.

COMPARATIVE EXAMPLE B

Combine 14 g of the disodium salt of 5-CNAC and 0.56 g of CabOSil and sieve through a 40 mesh screen. 0.3 g of the 5-CNAC disodium/CabOSil mixture, 0.028 g salmon calcitonin, pre-screened through a 40 mesh screen, and 0.56 g of Ac-Di-Sol, pre-screened through a 30 mesh screen are combined in a 1 quart V-blender shell. The mixture is blended for two minutes. Approximately 14.3 g of the 5-CNAC disodium/Cab-O-Sil mixture is added geometrically to the V-blender shell and mixed for two minutes after each addition (approximately 0.8, 1.7, 3.2, and 8.6 g are added successively). 12.43 g of Avicel PH 102 and 0.42 g of magnesium stearate, pre-screened through a 40 mesh screen are added to the V-blender shell and mixed for 5 minutes. The final blend is then screened through a 40 mesh screen and is compressed into tablets using, e.g. a Manesty F3 press. The tablet weights are approximately 400 mg.

COMPARATIVE EXAMPLE C 0.1224 of salmon calcitonin, pre-screened through a 40 mesh screen, 30 g of 5-CNAC disodium salt, pre-screened through a 35 mesh screen, and 4 g of Ac-Di-Sol are placed in a 500 mL Pyrex® jar and are mixed using a Turbula mixer for 2 minutes at a speed of 46 RPM. An additional 31.35 g of 5-CNAC disodium salt, pre-screened through a 35 mesh screen, and 15 g of Avicel PH 102 are added to the jar and are mixed for a period of 8 minutes at a speed of 46 RPM. 2 g of CabOSil and 16.15 g of Avicel are combined and are screened through an 18 mesh screen. The CabOSil/Avicel mixture is added to the jar and is mixed for 5 minutes at a speed of 46 RPM. 1.5 g of magnesium stearate is screened into the jar using a 35 mesh screen and is blended for 2 minutes at a speed of 46 RPM. The final blend is compressed into tablets using a Manesty B3B tablet press. The tablet weights are approximately 400 mg.

COMPARATIVE EXAMPLE D 18 kg of Water for Injection and 0.16 kg of sodium hydroxide, NF, are added to a vessel and mixed until dissolved. 0.800 kg of the free acid of 5-CNAC is added to the vessel and stirred at 400–600 RPM for a minimum of 10 minutes. The pH of the vessel is adjusted to approximately 8.5 using 10 N sodium hydroxide. The vessel is stirred for a minimum of 10 minutes after each addition of 10 N sodium hydroxide. The 10 N sodium hydroxide is prepared by adding 40 g of sodium hydroxide, NF, to 100 mL of Water for Injection. The final weight of the compounded solution is adjusted to 20.320 kg by the addition Water for injection (density 1.016). The vessel is stirred at 400–600 RPM for a minimum of 30 minutes. The compounded solution is filtered into another vessel using a peristaltic pump, silicone tubing, and a DuraPore 0.45 µm MPHL membrane capsule filter. A phosphate buffer solution is prepared by adding 13.8 g of monosodium phosphate monohydrate, USP to 900 g of Water For Injection and adjusting to a pH of 4.0 utilizing a 1.0 N phosphoric acid solution. The phosphoric acid solution is prepared by adding 0.96 g of phosphoric acid, NF, to 25 mL of Water for injection. The final weight of the phosphate buffer solution is adjusted to 1007 g (density 1.007) using Water for Injection and is stirred for 5 minutes.

A buffered salmon calcitonin solution is prepared by adding 1.6 g of salmon calcitonin to 660 g of the phosphate buffer solution. The final weight of the solution is adjusted to a final weight of 806.4 g (density 1.008) using the phosphate buffer solution and mixed for a minimum of 5 minutes at a speed of 250 RPM or less.

0.800 kg of the buffered salmon calcitonin solution is added dropwise to 20 kg of 5-CNAC solution with constant mixing at a speed of 250 RPM or less for a minimum of 5 minutes. Approximately 0.75 L of the salmon calcitonin/5-CNAC solution is filled into stainless steel lyophilization trays (30.5×30.5 cm) for a final solution depth of 0.8–0.9 cm. Approximately 29 trays are filled with 21.75 L of salmon calcitonin/5-CNAC solution. The trays are placed into an Edwards freeze dryer and lyophilized according to the following procedure:
1. When trays are loaded and the Reeze dryer is sealed, the shelves are cooled at a rate of 1° C./minute.
2. Once the shelf temperature reaches −45° C., maintain the shelf temperature at −45° C. for a minimum of 120 minutes.
3. Cool the condenser to −50° C. or below.
4. Evacuate the chamber and when a vacuum of 300 microns is maintained, raise the shelf temperature to −30° C. at a rate of 1° C. per minute.
5. Maintain the shelf temperature at −30° C. for 180 minutes.
6. Reduce the pressure in the chamber to 200 microns and when a vacuum of 200 microns is maintained, raise the shelf temperature to −20° C. at a rate of 1° C. per minute.
7. Maintain the shelf temperature at −20° C. for 200 minutes.
8. Raise the shelf temperature to −10° C. at a rate of 1° C. per minute.
9. Maintain the shelf temperature at −10° C. for 360 minutes.
10. Raise the shelf temperature to 0° C. at a rate of 1° C. per minute.
11. Maintain the shelf temperature at 0° C. for 720 minutes.
12. Reduce the pressure in the chamber to 100 microns and when a vacuum of 100 microns is maintained, raise the shelf temperature to +10° C. at a rate of 1° C. per minute.
13. Maintain the shelf temperature at +10° C. for 540 minutes.
14. Raise the shelf temperature to +25° C. at a rate of 1° C. per minute.
15. Maintain the shelf temperature at +25° C. for 440 minutes.
16. Release the vacuum and unload trays.

The colyophilized salmon calcitonin/5-CNAC is removed from the trays and stored in polyethylene and foils bags under refrigeration. Approximately 400 mg of colyophilized material is filed into capsules (size AA) for administration.

EXAMPLE 2

Primate Administration

The tablets or capsules prepared in Example 1 are administered to Rhesus monkeys as follows: four to six monkeys in a group were each dosed with either one capsule or two tablets of Example 1 as follows:

The Rhesus monkeys fast overnight prior to dosing and are restrained in chairs fully conscious, for the duration of the study period. The capsules or tablets are administered via a gavage tube followed by 10 mL of water.

Blood samples are collected at 0.25, 0.5, 0.75, 1, 1.5, 2, 3, 4, 5, and 6 hours after administration. Plasma salmon calcitonin is determined by radioimmunoassay. The primate plasma salmon calcitonin (sCT) results from each group of monkeys is averaged and the maximum mean plasma calcitonin concentration and area under the curve (AUC) results are calculated and reported in Table 2.

TABLE 2

| Dosage Form | sCT Cmax (pg/mL) | sCT AUC |
|---|---|---|
| COMPARATIVE EXAMPLE D | 415 | 792.4 |
| COMPARATIVE EXAMPLE B | 457 | 992.5 |
| COMPARATIVE EXAMPLE C | 329 | 797 |
| EXAMPLE A | 2420 | 4400 |

As can be seen from the data in Table 2, the salmon calcitonin Cmax and the salmon calcitonin AUC are much greater for the composition according to the present invention containing the crospovidone (Example A) versus the comparative compositions which do not contain crospovidone, resulting in greatly enhanced oral bioavailability of the formulations according to the instant invention.

EXAMPLE 3

Accelerated Stability Testing

Tablets containing 0.065 mg, 0.400 mg, and 2.500 mg sCT are prepared according to Comparative Example C and Example A, respectively, with the sCT and Avicel adjusted in order to obtain the target strengths. The tablets are placed in a HDPE bottle with a desiccant, which is induction sealed and capped. Accelerated stability tests are conducted by placing the stability samples in environmental chambers at 25° C. and 60% relative humidity. The samples are pulled at the specified time points, i.e. at 3, 4 and 6 weeks, and analyzed for sCT by HPLC. The results are shown in Table 3.

Comparison of Comparative Example C after 4 weeks (about a 10% decrease in sCT assay) with Example A according to the present invention after 6 weeks (about a 5% decrease in sCT assay), both at room temperature, demonstrates that the formulation according to the instant invention results in improved stability of the tablets prepared according to the instant invention.

EXAMPLE 4

Tablet disintegration of the solid formulations was determined by preparing tablets as per Example 1 containing 60% 5-CNAC Disodium, 29% Avicel, 1% Magnesium Stearate, but excluding the sCT. Tablet disintegration was determined according to the USP Disintegration Test <701> while tablet hardness was determined using a calibrated Vector/Schleuniger 6D Tablet Hardness Tester. The results are shown in Table 4.

TABLE 4

| Excipient | Content | Hardness | Disintegration | Hardness | Disintegration |
|---|---|---|---|---|---|
| Ac-Di-Sol | 10% | 5.7 Kp* | 1.1–1.4 min | 10.1 Kp | 5.6–6.5 min |
| Explotab | 10% | 6.9 Kp | 2.6–3.3 min | 10.3 Kp | 6.5–7.5 min |
| Polyplasdone XL | 10% | 7.3 Kp | 0.6–0.8 min | 10.5 Kp | 2.4–2.7 min |
| Ac-Di-Sol(Cab-O-Sil)* | 10% | 6.3 Kp | 4.3–5.3 min | 10.3 Kp | 7.3–8.0 min |

*Kp = Kilopascals

The results in Table 4 indicate that the use of Polyplasdone XL (crospovidone) in combination with the 5-CNAC produced the fastest disintegration relative to tablets prepared using 5-CNAC in combination with other excipients indicating improved release of the pharmacologically active agent from solid formulations according to the instant invention.

EXAMPLE 5

Chemical Stability

Samples for extreme stress stability testing are prepared by placing tablets (prepared analogously to those in Example 1, above, using the ratio of ingredients indicated in Table 5) in a capped amber bottle. Accelerated stability tests are conducted by placing the samples in a calibrated oven at 60° C. Samples are analysed for sCT initially and after either 3 or 4 days as specified by HPLC. The results are shown in Table 5.

TABLE 3

| | 0.065 mg Tablet | | 0.400 mg Tablet | | 2.500 mg Tablet | |
|---|---|---|---|---|---|---|
| sCT Assay 25° C./60% RH | Comparative Example C | Example A | Comparative Example C | Example A | Comparative Example C | Example A |
| 0 Time | 93.5% | 100.9% | 94.3% | 103.0% | 100.3% | 98.0% |
| 3 Weeks | — | 97.4% | — | 98.8% | — | — |
| 4 Weeks | 84.2% | — | 88.8% | — | 91.5% | 100.2% |
| 6 Weeks | — | 95.2% | — | 96.9% | — | — |

TABLE 5

| Excipients (0.4 mg sCT/200 mg 5-CNAC Disodium) | 60° C. | Initial sCT Assay | Stress sCT Assay | % Change |
|---|---|---|---|---|
| Ac-Di-Sol, Cab-O-Sil, Avicel, Mg. Stearate (COMPARATIVE EXAMPLE C) | 3 Days | 94.0% | 12.3% | −81.7% |
| 10% PolyplasdoneXL-10, Avicel, Mg. Stearate (EXAMPLE A) | 4 Days | 98.3% | 86.5% | −11.8% |

As can be seen from Table 5, the chemical stability of sCT under extreme stress conditions was improved with the formulation of the instant invention (Example F) containing crospovidone (Polyplasdone XL-10) when compared with the comparative formulation without crospovidone.

The foregoing clearly shows that the compositions according to the instant invention have considerably improved oral bioavailability of active agent, particularly calcitonin, relative to other oral formulations, good disintegration rates and excellent stability.

The foregoing embodiments and examples are given merely to illustrate the instant invention and are not intended to be limiting. Numerous other embodiments and variations are within the scope of the invention and readily accessible to those skilled in the art.

We claim:

1. A solid salmon calcitonin comprising
   a. a pharmacologically active agent,
   b. crospovidone or povidone,
   c. 5CNAC,
   d. optionally, microcrystalline cellulose, and
   e. optionally, magnesium stearate
   wherein, said solid salmon calcitonin provides enhanced oral bioavailability of said pharmacologically active agent.

2. The solid pharmaceutical composition of claim 1 wherein, said salmon calcitonin is present in an amount of from 0.05–70% by weight relative to the total weight of the overall pharmaceutical composition; said crospovidone or povidone is present in an amount of from 0.5–50% by weight relative to the total weight of the overall pharmaceutical composition; and said 5-CNAC is present in an amount of from 2.5–99.4% by weight relative to the total weight of the overall pharmaceutical composition.

3. The solid pharmaceutical composition of claim 2 wherein
   the crospovidone or povidone is present in an amount of from 2–25% by weight relative to the total weight of the overall pharmaceutical composition.

* * * * *

UNITED STATES PATENT AND TRADEMARK OFFICE
CERTIFICATE OF CORRECTION

PATENT NO. : 7,049,283 B2  Page 1 of 1
APPLICATION NO. : 10/006311
DATED : May 23, 2006
INVENTOR(S) : Joseph M. Ault It is certified that error appears in the above-identified patent and that said Letters Patent is hereby corrected as shown below:

Column 11

Claim 1, line 28, delete "salmon calcitonin" and insert --pharmaceutical composition--

Claim 1, line 29, delete "pharmacologically active agent" and insert --salmon calcitonin--

Column 12

Claim 1, line 14, delete "salmon calcitonin" and insert --pharmaceutical composition--

Claim 1, line 15, delete "pharmacologically active agent" and insert --salmon calcitonin--

Signed and Sealed this

Sixteenth Day of September, 2008

JON W. DUDAS
*Director of the United States Patent and Trademark Office*